(12) United States Patent
Rosemeyer (10) Patent No.: US 7,914,991 B2
(45) Date of Patent: Mar. 29, 2011

(54) NUCLEOLIPIDS AND USE THEREOF, AND DEVICES FOR NUCLEIC ACID ANALYSIS

(76) Inventor: Helmut Rosemeyer, Osnabruck (DE)

( * ) Notice: Subject to any disclaimer, the term of this patent is extended or adjusted under 35 U.S.C. 154(b) by 150 days.

(21) Appl. No.: 11/917,230

(22) PCT Filed: Jun. 22, 2006

(86) PCT No.: PCT/EP2006/006013
§ 371 (c)(1),
(2), (4) Date: Jul. 2, 2008

(87) PCT Pub. No.: WO2006/136411
PCT Pub. Date: Dec. 28, 2006

(65) Prior Publication Data
US 2009/0163372 A1    Jun. 25, 2009

(30) Foreign Application Priority Data
Jun. 22, 2005 (EP) .................................. 05013432

(51) Int. Cl.
*C12Q 1/68* (2006.01)
*C12Q 1/70* (2006.01)
*C07H 21/02* (2006.01)
*B01L 3/00* (2006.01)

(52) U.S. Cl. .................. 435/6; 435/5; 435/7.1; 435/7.2; 536/23.1; 536/24.3; 536/25.3; 536/26.6; 422/61

(58) Field of Classification Search .................. 435/5, 6, 435/7.1, 7.2; 536/23.1, 24.3, 25.3, 26.6; 422/61
See application file for complete search history.

(56) References Cited

U.S. PATENT DOCUMENTS
5,976,567 A * 11/1999 Wheeler et al. ............... 424/450

OTHER PUBLICATIONS

Miao et al., Molecular Recognition of Nucleoliplid Monolayers of 1-(2- Octadecyloxycarbonylethyl) cytosine to Guanosine at the Air-water Interface and Langmuir-Blodgett Films, Bd. 19, 17, May 2003, Sieten 5389-5396.
Huang et al. Molecular Recognition of Nucleolipid Amphiphile Ocadecanoyl Ester of 1-(2-carboxyethyl) adenine to the complemenetary nucleobases. Part IBd. 326, Nr. 1-2, Aug. 4, 1998, Seiten 217-222.
Rosemeyer et al. A Nucleolipid with antiviral Acycloguanosine as head Group Synthesis and Liposome Formation, Bd. 24, Nr. 6, 1985, Seiten 501-502.
Davis et al., Structured thin Films as Functional Components within Biosensors, Bd. 21, No. 1, Nov. 18, 2004, Seiten 1-20.

* cited by examiner

*Primary Examiner* — Jezia Riley
(74) *Attorney, Agent, or Firm* — Whitham Curtis Christofferson & Cook, PC (57) ABSTRACT

The invention relates to a method for isolating and/or identifying known or unknown, nucleic acid sequences (target sequences) which are marked, optionally, with reporter groups, by base specific hybridisation with, essentially, complementary sequences, which belong to a library or sequences. The sample sequences are characterised in that they support, on one of the termini thereof (5'-ends or 3'-ends, preferably on 5'-ends), a single double or multi-chained lipid part, which spreads in a monomolecular layer on a liquid gas or liquid-liquid phase boundary layer. The invention also relates to a system for detecting or isolating nucleic acids.

14 Claims, 5 Drawing Sheets

F: Functional group
L: linker atom/atom group
K: connector

NUCLEOLIPIDS AND USE THEREOF, AND DEVICES FOR NUCLEIC ACID ANALYSIS

Subject of the invention is a method for the isolation and/or identification of known or unknown sequences of nucleic acids (target sequences) optionally marked with reporter groups by base specific hybridation with, essentially, complementary sequences (in the following referred to as sample oligo-nucleotides, sample sequences or sample nucleic acids), which belong to a library of sequences. The sample sequences are characterized in that they all carry single-, double or multiple chained lipid component on one of their termini (5' or 3'-end, preferably the 5' end) which enables them to build a spreading of a mono molecular layer at a liquid-gas or a liquid-liquid phase interface.

BACKGROUND OF THE INVENTION

Nucleic acids are of central importance in living nature since they are the carriers and transmitters of genetic information. The increasing knowledge of basic molecular biological mechanisms in the last few years made it possible to conduct genetic engineering. This technology allows new possibilities for example in the fields of medical diagnostics and therapy as well as plant breeding.

The verification of nucleic acids and fragments of nucleic acids was and still is an important tool for the explanation of those relations and for the answer of the problems, namely concerning their specific identification as well as their specific sequence—their primary structure. Furthermore, a part of molecular biological work is the isolation of nucleic acid sequences, such as the purification and subsequent processing of selected nucleic acids.

The specific traceability of nucleic acids is based on the property of the molecules to build base pairs with other nucleic acids by the formation of hydrogen bonds—i.e. to hybridise. The analysis of genes or gene segments is currently based on DNA—chips. Those chips, arrays or DNA-microarrays are made up of a solid carrier (a glass object plate) on which single-stranded DNA-molecules with a known sequence are attached in a regular pattern. Those nucleic acid chips are either produced by
  (i) direct synthesis on the solid carrier using masks and a photo lithographic procedure
  (ii) or prefabricated and terminally functionalized samples of nucleic acids are chemically attached to activated surfaces by covalent bonds.

The DNA analysis involves multiple steps:
  (i) preparation of the sample (extraction, PCR etc.)
  (ii) hybridisation on the chip
  (iii) stringent washing
  (iv) detection
  (v) bio informatic analysis Both ways of producing DNA-chips are afflicted with numerous problems. The first method calls for the synthesis of the oligo-nucleotides directly on the carrier and includes a comprehensive amount of deprotection reactions and washing. This constitutes a complex method, especially when the array includes a multitude of different nucleic acid samples. In case of the second method for example the solid surface—usually a glass plate—must be activated with functional groups in a complicated manner. Only then it is possible to apply the likewise premade functionalised nucleic acids with a known sequence. This application ("spotting") is also problematic and requires expensive and complicated equipment, so called "microarrayers". What follows is a chemical reaction between the ready-made functionalised nucleic acids and the activated functional groups on the surface of the array in order to achieve a covalent bond between the array and the nucleic acid.

Today, the common method for the isolation of nucleic acids comprises the use of chaotropic compounds in combination with solid materials like silica, silica derivatives or magnetic particles. The disadvantage of these methods is a complex process for isolation with many steps of washing and centrifugation.

Furthermore, the isolation of mRNA using oligo-nucleotides requires a pretreatment of the solid materials either to allow a direct covalent bonding or an indirect coupling of the oligo-molecules with the solid materials.

Another alternative is the purification with the help of membranes.

It is one object of the present invention to provide a new, much easier and cheaper method for the analysis of nucleic acids which avoids the complicated chemical coupling reactions with the carrier material.

Another object of the present invention is the preparation of new compounds which can especially be used in procedures for the analysis of nucleic acids.

SUMMARY OF THE INVENTION

The present invention provides new nucleolipids which include a lipophilic (also referred to as lipid) and a nucleoside-, oligo- or polynucleotide unit (moiety), respectively. Those two components are connected by a linker (e.g. containing a nitrogen atom), a spacer and a functional unit which is called a connector (e.g. a phosphoric acid diester moiety). The connector is a phosphoric acid diester compound which is formed between the lipid part and the nucleotide part, when a phosphonate- or phosphoramidite group of a compound with a lipophilic and a functional portion react with the 3' or 5' OH— group of a nucleoside, e.g. the 3' or 5' end of an oligo-nucleotide or a poly-nucleotide. The current invention also provides compounds which can be used for the synthesis of the nucleolipids mentioned above. Those compounds, also called reactive lipids in the following, include a lipohilic and a functional moiety which are connected via a linker and a spacer, characterized in that the linker, consisting of an amine group or a molecule with at least two functional groups, is directly connected with the lipophilic moiety and the functional moiety, being a phosphonate or a phosphoramidite group, whereby said functional moiety is directly linked to a spacer (containing at least one carbon containing group) via an oxygen atom. The present invention also provides a system for nucleic acid analysis, including a device which consists of a lower part which can contain a liquid phase and an upper part which is not permanently attached to the lower part, said upper part which is insertable into the lower part contains at least two compartments separated from each other and these compartments are designed to extend from the upper to the lower side of the upper part. The system also includes nucleolipids, especially these nucleolipids according to the present invention, which are being spread at the phase interface within the compartments.

Finally the invention relates to a method for the isolation of nucleic acids from samples and methods for detection of nucleic acids within samples, respectively. The present invention also covers arrays like DNA-chips used for the analysis of nucleic acids using nucleolipids as sample sequences.

SHORT DESCRIPTION OF THE FIGURES

FIG. 1 illustrates a schematic design of the compounds according to the invention. (A) shows a compound according to the invention, the reactive lipid, containing one or more lipophilic moieties (lipids also referred to as F in the following), the functional moiety (P) and between them the linker (L) and spacer (S). The scheme shows different versions of the reactive lipids containing one as well as double or multiple chained lipids in the compounds.

FIG. 1 (B) depicts the nucleolipids according to the invention. The scheme also shows different varieties of the nucleolipids containing one, two and more chained lipid moieties. The connector (K) as the remaining part of the functional group connects the nucleotide with the spacer with the attached lipohilic portion.

FIG. 2 (A) shows the synthesis of a reactive lipid according to the invention, have a derivative of a phosphoramidite (see example 1). (B) depicts branched reactive lipids according to the invention (compounds 4+5).

DETAILED DESCRIPTION OF THE INVENTION

This invention concerns nucleolipids as well as intermediate products used for their production. A nucleolipid is defined as a chemical compound including a nucleoside, nucleotide or nucleobase and a single, double or multi chained lipid. The surface active behaviour of those "chimeric" molecules has been generally examined with Langmuir-Blodgett equipment. It has been shown that these compounds orient themselves at a phase layer (interface) in such a way, that the hydrophobic part of the molecule (lipid) points into the gaseous phase while the hydropilic head group points into the liquid subphase.

The general synthesis of nucleolipids and their spreading behaviour at a phase layer (interface) has been described in the art. New nucleolipids are described in this invention which are especially suitable for the analysis of nucleic acids.

The nucleolipids of this invention contain a lipohilic and a functional moiety which are connected to each other via a linker and a spacer, as well as a nucleoside-, oligonucleotide- or polynucleotide part. The linker of this compound is an amine group or a molecule with at least two functional groups and is connected with the lipophilic moiety while the nucleoside-, oligonucleotide- or polynucleotide moiety is connected to the spacer via the functional unit of a phosphoric acid diester.

In a preferred embodiment of the present invention, the nucleolipids according to the present invention contain an oligonucleotide structure between 2 and 100 nucleotides.

According to the present invention, nucleic acids cover both desoxy-, as well as ribonucleic acids. They are compounds with a length of at least 2, like at least 4, 6, 8, 10 or at least 20 or at least 30 bases.

The term "nucleic acids" also covers PNA molecules or similar well known variations of DNA or RNA molecules as described in the art. The bases within those nucleic acids may be natural bases or modified bases found in nature or manmade.

The present invention also covers compounds, reactive lipids, which form a nucleolipid when reacting with a nucleoside, an oligonucleotide or a polynucleotide. Those reactive lipids comprise a lipophilic moiety and a functional moiety which are connected to each other via a linker and a spacer with the linker being an amine group or a molecule with at least two functional groups connecting to the lipophilic moiety via covalent bonds while the functional group being a phosphonate or a phosphoramidite group, whereby the functional group is covalently connected to the spacer, which contains at least one carbon group, via an oxygen atom. The composition of a compound according to the invention has the following structure:

$$F_n\text{—}S\text{—}OPX_1X_2 \qquad (1)$$

where F is a lipophilic moiety;
n is an integer with $n \geq 1$;
L is a tertiary amine-, glycol- or glycerin-residue;
S is a spacer, consisting of at least one carbon containing group;
$OPX_1X_2$ represents a phosphonate- or phosphoramidite group, where either $X_1$ or $X_2$ is a protecting group while the other group being the leaving group when connecting with a nucleoside, which can be a part of an oligonucleotide or polynucleotide.

In a preferred embodiment the compound has the following general formula (2):

$$\begin{array}{c} F \\ \diagdown \\ \phantom{F}L\text{-}S\text{-}OPX_1X_2 \\ \diagup \\ F \end{array} \qquad (2)$$

where F, L, S and $OPX_1X_2$ are as defined above.

Preferably, n is an integer selected from 1, 2, 3, 4, 5, in particular, n is 1 or 2.

Figure 2A:
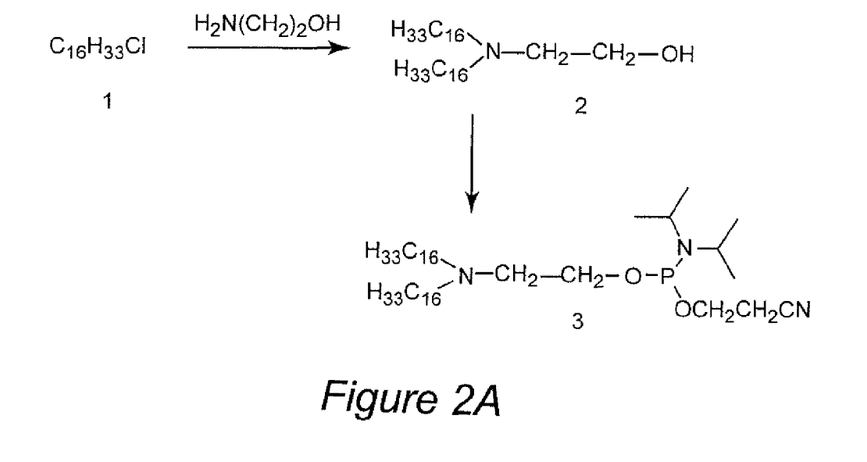
Figure 2B:
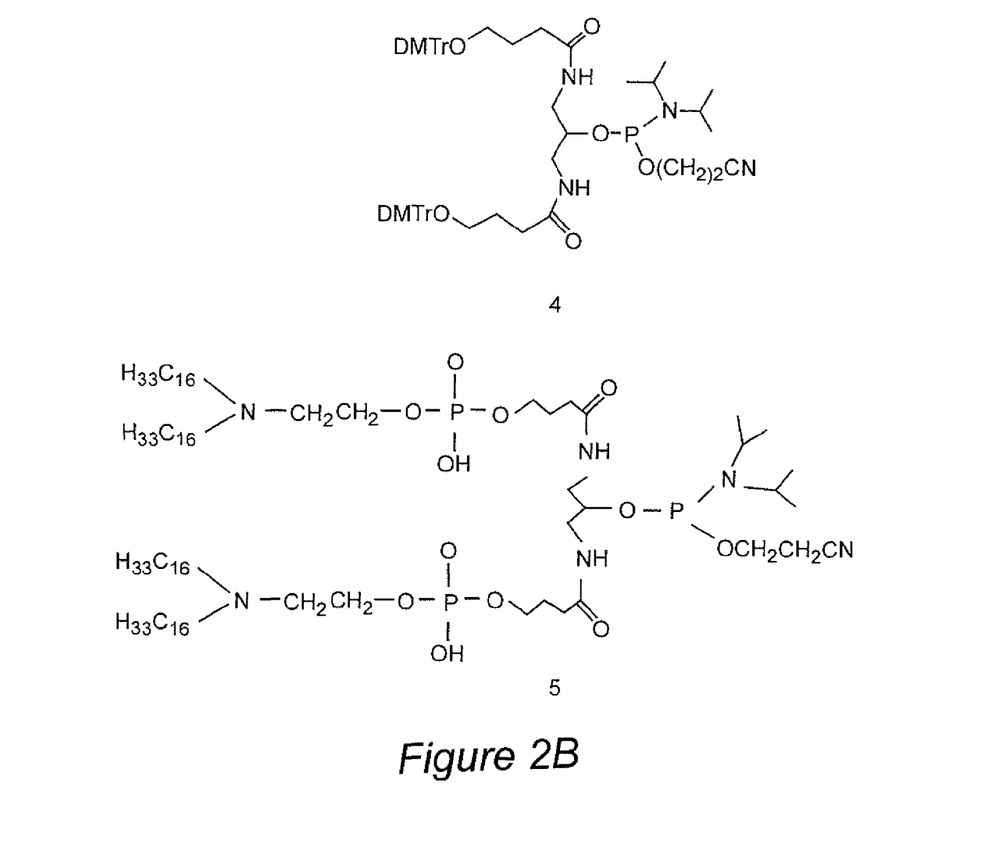

In a preferred embodiment, the lipophilic moiety contains a carbon structure with 10 to 40 carbon atoms, preferably with 12 to 40 or with 10 to 20 carbon atoms. The carbon structure may have one or more conjugated or not conjugated double or triple bonds. In case the compound comprises multiple chained lipids, like double chained lipids, the lipohilic moiety may be the same or different. The lipophilic moiety may be any lipid which are generally insoluble in water. Examples are: hydrocarbons like squalenes and carotinoids; alcohols like washing alcohols and cholesterol; ethers, carboxylic acids, saturated and unsaturated fatty acids; terpenes and steroids as well as lipohilic vitamins like vitamin D, E and D2 etc. The number of the lipid groups can be increased by using dentritic branching molecules in order to augment the lipophilic character of the lipid-nucleic acid conjugates (see compound 5 in FIG. 2). It is due to the branching molecules, called doubling or tripling synthons (Loakes D.: Organophosphorous Chemistry, Vol. 33, 2003, 204ff), that the number of the lipophilic chains in the lipophilic section may be increased and thus augmenting the lipophilicty of the nucleolipid altogether.

An alternative method in order to avoid a "pulling" effect of the nucleic acid moiety into the hydrophilic phase is the use of for example silicone oil or other oils instead of air which increases the lipophily of the lipophilic phase. It is preferable that the HLB values of both phases of the system differ as much as possible.

It is preferred that the linker-group consists of a tertiary amine. Another preferred linker group is a glycerin- or a glycol-residue. Other linker-groups are for example secondary amines, polyvalent alcohols such as trivalent or tetravalent alcohols, especially 1,3,5-trihydroxypentane or 1,4,7-trihydroxyheptane or pentaerythrite.

The spacer contains at least one carbon containing group and is preferably an alkyl- or alkenyl-group with 1 to 10 carbon atoms; an ethylene group is especially preferred. The linker can of course also contain other groups, as long as they do not interfere the spreading of the nucleolipids according to the present invention at a surface layer.

The functional group is preferably a phosphoramidite group.

A particularly preferred embodiment of the compound according to the present invention has a tertiary amine as a linker, a $C_2$-$C_8$ alkyl group as a spacer, a phosphoramidite group as a functional group, and the lipids comprise a hydrocarbon chain with 12 to 40 carbon atoms which can contain one or multiple conjugated or not conjugated double bonds, whereby the carbon chains may be identical or different from each other.

Another preferred embodiment has a glycol residue as a linker, a $C_2$-$C_8$ alkyl group as a spacer, a phosphoramidite residue as a functional group and the lipids comprise hydrocarbon chains with 12 to 40 carbon atoms which can contain one or multiple conjugated or not conjugated double bonds, whereby the carbon chains may be identical or different from each other.

Finally, another preferred embodiment contains a glycerin residue as a linker, a $C_2$-$C_8$ alkyl group as a spacer, a phosphoramidite residue as a functional group and the lipids comprise hydrocarbon chains with 12 to 40 carbon atoms which can contain one or multiple conjugated or not conjugated double bonds, whereby the carbon chains may be identical or different from each other.

Nucleolipids are synthesised using the compounds according to the present invention according to known methods. Preferred embodiments of the nucleolipids according to the present invention contain those that were produced with preferred embodiments of reactive lipids according to the invention. An especially preferred embodiment has the lipophilic moiety connected to the 5' end of the oligo- or poly-nucleotide via the linker, spacer and a phosphoric acid diester group.

This invention also covers a method for synthesising modified nucleotides, oligonucleotides or polynucleotides and comprising the step of the reaction of the reactive lipids according to the present invention with nucleosides, oligonucleotides or polynucleotides which are protected, except at one OH group.

Figure 1A:
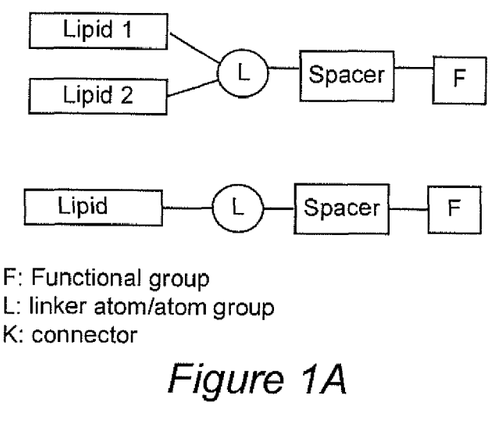
Figure 1B:
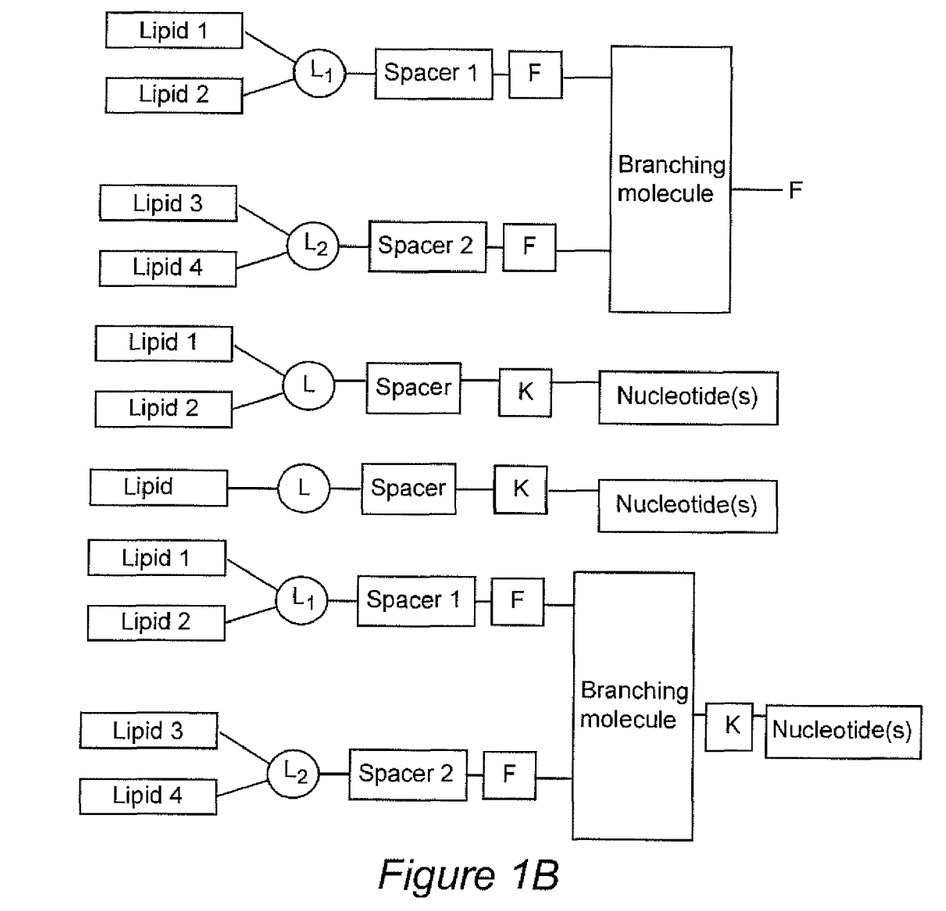

The lipid/sample nucleic acid-conjugates are prepared by preparing the single strands of sample nucleic acids using methods well known to the artisan. Preferably, an automatic solid phase synthesis using the phosphoramidite- or the phosphonate-method, is applied. The lipid moiety is the last component used during the routine automatic synthesis using a compound according to the invention and is for example a phosphoramidite derivative or also an appropriate phosphonate derivative. As already mentioned, the lipid component may have different structures, examples thereof are shown in FIG. 1.

The present invention also covers a method for the identification of nucleic acids. This method includes the steps of providing a sample potentially containing nucleic acids, providing nucleolipids according to the present invention which hybridise with the nucleic acid to be determined under hybridising conditions and contacting the nucleolipids with the sample under hybridising conditions, thus, forming a hybridised product of a nucleic acid contained in the sample and the nucleolipid and detecting said hybridisation product. In this context, the term "hybridisation" or "hybridising conditions" means the hybridisation under conventional hybridising conditions, especially under stringent conditions as described for example by Sambrook and Russell (Molecular cloning: a laboratory manual, CSH Press. Cold Spring Harbor, N.Y., USA, 2001). The term "hybridisation" means in an especially preferred embodiment that the hybridisation takes place under the following conditions:

Hybridisation buffer: 2×SSC; 10×Denhardt-solution (Ficoll 400+PEG+BSA; ratio 1:1:1); 0.1% SDS; 5 mMol EDTA; 50 mMol $Na_2HPO_4$; 250 µg/ml herring-sperm DNA; 50 µg/ml tRNA; or 0.25 mol sodium phosphate buffer, pH 7.2; 1 mMol EDTA, 7% SDS Hybridising temperature: T=60° C.

Washing buffer: 2×SSC; 0.1% SDS;

Washing temperature: T=60° C.

In a further preferred embodiment the term "under hybridising conditions" means formation of multiple stranded hybridisation products under the following conditions:

Hybridisation buffer: 10 mM Na-Cacodylate, 10 mM $MgCl_2$, 100 mM NaCl or 10 mM Na-Cacodylate, 100 mM $MgCl_2$, 1 M NaCl (the latter for increase low Tm-values)

Hybridisation temperature: room temperature, individually between room temperature and 60° C. depending on the length and the composition of the target and sample sequences to be hybridized washing buffer: see above washing temperature: room temperature In a particular preferred embodiment of the present invention, the sample-sequence only hybridises with the target-sequence under hybridising conditions in which the sample-sequence is complementary to the target-sequence. This is of great importance when single mutations are to be identified like for example in the pharmacogenetic field.

This invention also includes a method for detecting the presence or absence of nucleic acids containing specific sequences within a sample and includes the following steps:

bringing the sample in contact with the nucleolipids according to the present invention having oligo- or poly-nucleotide moieties. At least one of these oligo- or poly-nucleotides must show a sequence substantially complementary to a specific sequence of nucleic acids contained in the sample, and detecting the formation of hybridising products of the nucleolipids according to the present invention and a specific sequence of nucleic acids within the sample (target-sequence) if contained within the sample.

The nucleic acid containing a specific sequence (target sequence) can be marked with a reporter group before using conventional, well known techniques. The skilled person is aware of many of those marker molecules, such as fluorescence dyes, radioactive markers, biotin etc.

In a preferred embodiment fluorescence dyes are used as reporter groups, for example fluorescein, a member of the Alexa- or Cy-dye-group.

In another embodiment, the method according to the present invention for determining the absence or presence of nucleic acids containing specific sequence within a sample is conducted in a way that the step of bringing into contact is conducted in multiple compartments which are separated from each other, whereby in each of said compartments a nucleic lipid having identical nucleic acid sequences is present, thus, the probe sequences present in a single compartment is identical and, in addition, different sequences are present in each of the separated compartments. Alternatively, in one compartment various nucleic lipids having different predetermined nucleic acid sequences may be present. It allows to analyse multiple samples.

During equilibration of the chemical equilibrium hybridization of the target nucleic acid with the corresponding sequence of a multitude of probe sequences occur. Optionally, the kinetics of hybridisation may be optimized by adjusting the temperature of the liquid phase. Optionally, non bonded target sequences may be removed by washing. Stirring of the solution containing the target sequences is preferred.

According to the invention, the identification of the hybridising products can be effected by testing for the reporter groups. When using a fluorescence dye as a reporter group, the measurement of the hybridising products is done by measuring the emitted fluorescence of this marker. In a preferred embodiment, the measurement of the reporter group is effected in the area of the liquid-gas boundary only. In another embodiment using two liquid phases (both liquids are only limited miscible or immiscible and they must form a phase boundary) allows the measurement of the reporter group at the liquid-liquid boundary between the two fluids.

The nucleolipids according to the present invention cannot only be used to identify nucleic acids within a sample but also to isolate nucleic acids from a sample containing nucleic acids. Therefore, this invention also covers a method for the isolation of nucleic acids from samples containing nucleic acids and includes the following steps a) bringing the nucleic acids containing sample into contact with the nucleolipid(s) comprising a lipophilic moiety and an oligo- or polynucleotide moiety, whereby the oligo- or polynucleotides allow the hybridisation with at least a part of the nucleic acids contained within the sample, and b) separation of the hybridising products from the other ingredients contained in the sample and, optionally, washing the hybridising products.

Preferably, the bringing into contact occurs in a first liquid phase. By adding a second liquid phase which builds a liquid-liquid boundary with the first liquid phase allowing a spreading of the nucleolipids in a mono-molecular layer in such a way that the lipophilic moiety reaches into the more lipophilic liquid phase, while the other part of the nucleolipid, hybridised with the complementary nucleic acid sequence, extends into the other fluid, the hybridising products can be separated from single stranded nucleic acids from the sample. If desired, the hybridising products can also be separated from the other ingredients contained within the sample and, optionally, be washed.

In a preferred embodiment of the present invention the nucleolipids are used for the isolation of RNA-molecules, especially siRNA, miRNA or mRNA. When isolating mRNA-molecules, the nucleotide moiety of the nucleolipid has a polydT-sequence. Of course, the isolation can also be based on other known sequences contained within the target-sequence.

In another preferred embodiment of the present invention certain types of nucleic acids, namely aptameres, may be used for the isolation method. In case aptameres are used as the nucleic acid moiety of the nucleolipids, purification of other molecules than nucleic acids, like for example proteins, is possible.

This invention also concerns kits for identifying nucleic acids which contain one or more of the nucleolipids according to the present invention. These kits contain instructions for the detection of nucleic acids and, if required, a second liquid phase which builds a liquid-liquid boundary with the liquid sample.

The nucleotides according to the present invention may also be used to produce arrays of nucleic acids. This means that the nucleolipids containing a lipid moiety and an oligonucleotide moiety can be utilised in nucleic acid arrays, so called DNA-chips. These DNA-chips can be used for example for the analysis of genes or sections of genes, in particular, in pharmacogenetic analyses. Those microarrays may now be produced with the help of the nucleolipids, according to the present invention, which in contrast to the conventional DNA-chips no longer requires complicated chemical procedures for activation of the solid surface and chemical fixation of the sample sequences on those surfaces.

Furthermore, the arrays according to the present invention have another advantage compared to the conventional arrays with permanent, i.e. covalently bound nucleic acid moieties, since they show spacial flexibility. When a hybridising product is formed, they require more space which requires a lateral displacement of the sample sequences. Since the nucleolipids are not connected to the solid plate by covalent bonds and the arrangement of the molecules at the boundary layer of a liquid-liquid system, respectively, the nucleolipids can move laterally thus enabling an optimum density for hybridisation at all times.

Therefore, this invention also concerns a system for the analysis of nucleic acids comprising a device like for example a DNA-chip or an array, comprising a lower section which may contain a liquid phase and an upper section which is not permanently attached to the lower part and which is insertable into the lower part, whereby the upper part has at least two compartments separated from each other and these compartments are formed from the upper to the lower side of the upper part. This makes it possible that e.g. the liquid phase in the lower section is able to exchange target nucleic acids contained within the phase of the upper section.

Preferably, the upper section has at least 4, 8, 16, 25, 64, 256, 384, etc. separated compartments.

Figure 4:
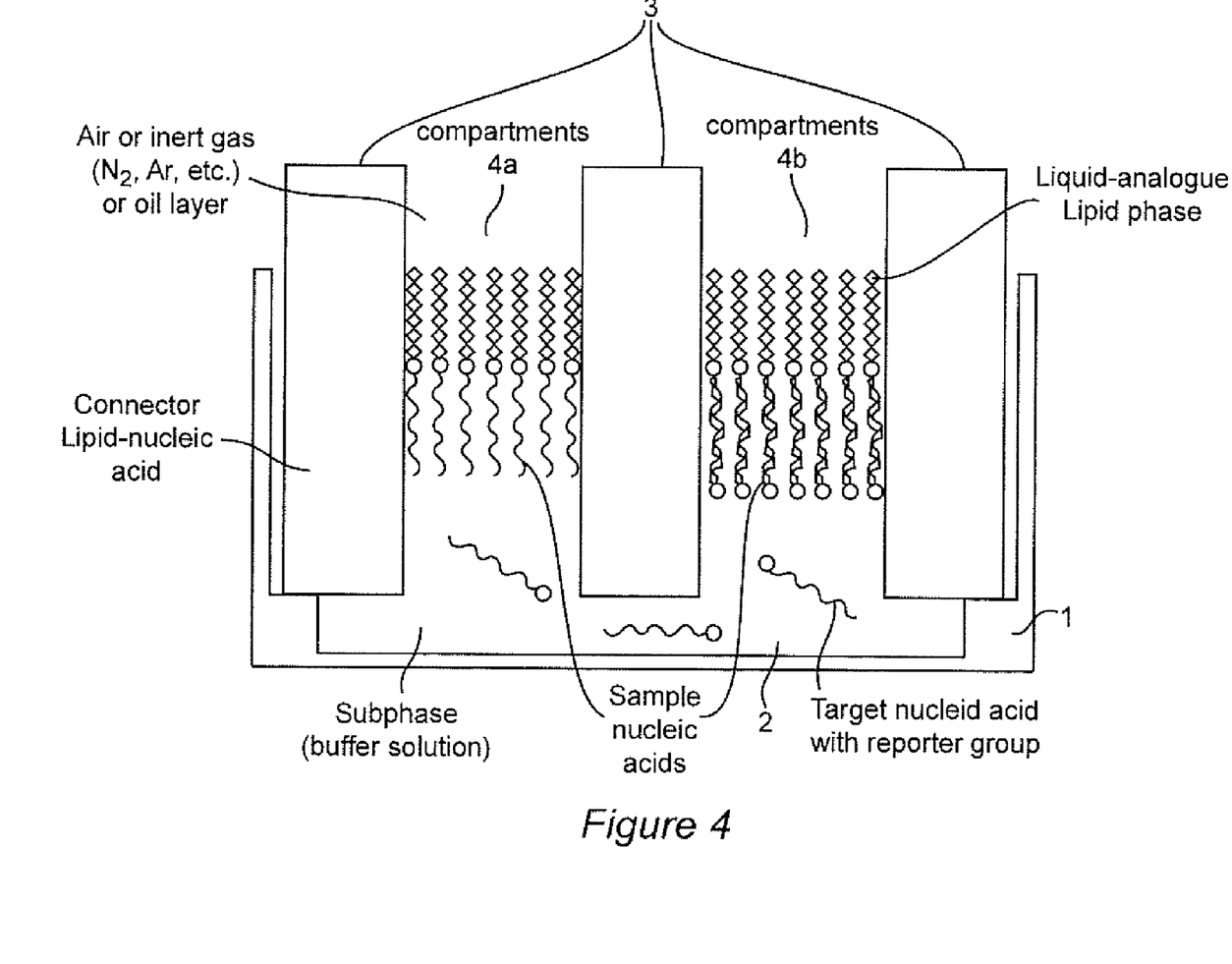
FIG. 4 shows a schematic drawing of the way the device according to the present invention works and depicts the method for identifying specific sequences (target nucleic acids) within a sample.

In a preferred embodiment of the device, the upper part is designed in such a way that when placed within the lower part the lower section of the lower part contains a joined liquid subphase which is not divided in single compartments. This is illustrated e.g. in FIG. 4. FIG. 4 shows a cross section of the device according to the present invention. The lower section 1 comprises an area which contains the first liquid phase 2. The upper section 3 separates the upper section of the first liquid phase into two compartments 4a and 4b which both contain the first liquid phase 2. The lower section of the liquid phase is not separated into different compartments by the upper section 3. Target nucleic acids including reporter groups are free to move in this first liquid phase. Optionally, a stirring device may be used in this lower section.

Compartments 4a and 4b contain the sample nucleic acids which are spreaded at the boundary layer built by the first liquid with a gas or a second fluid. The sample nucleic acids reach into the first liquid.

A specific detection of nucleic acids is possible by the use of nucleolipids and the device according to the present invention. In the following an example is given for the analysis of nucleic acids using the system according to the present invention comprising the nucleolipids and the device described above.

Figure 3:
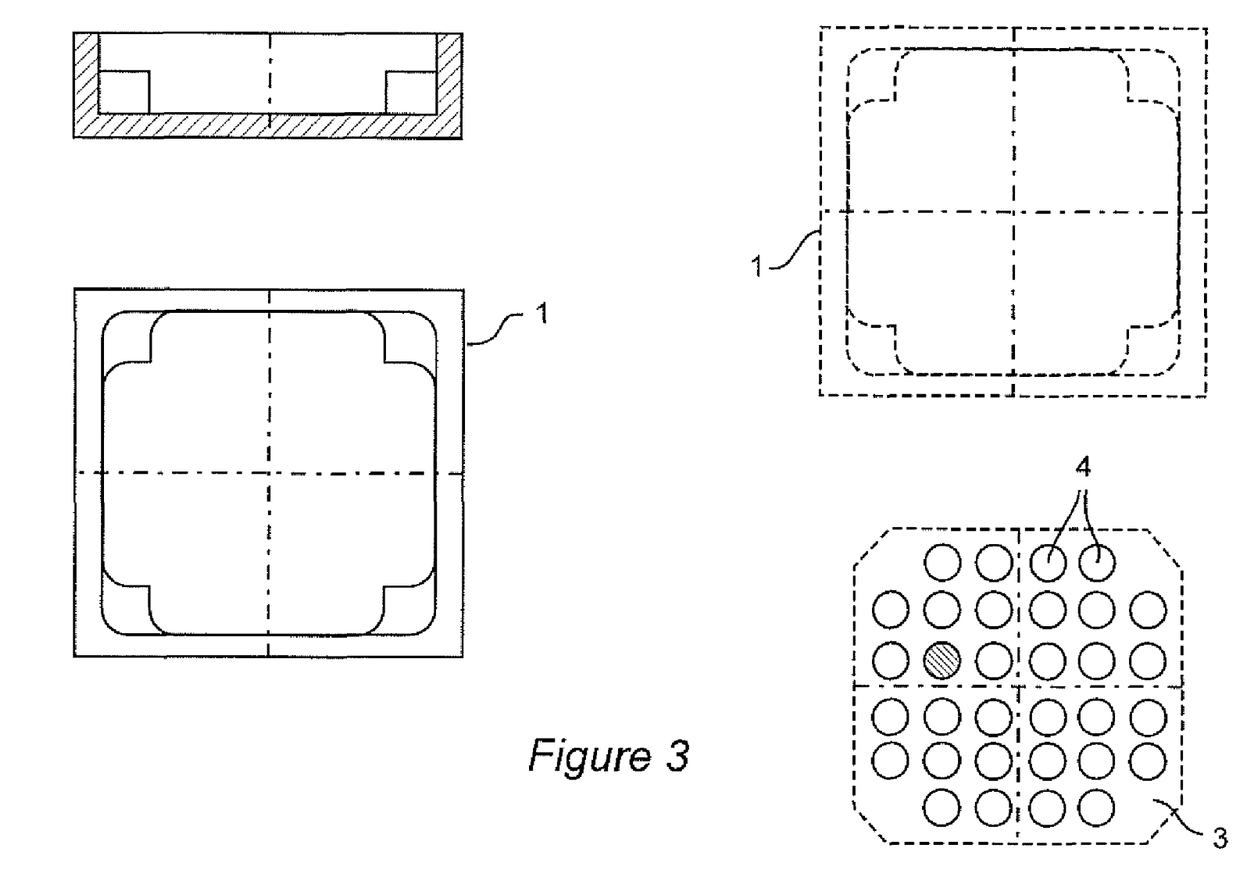
FIG. 3 represents a schematic drawing of a device for the analysis of DNA according to the invention.

The highly lipophilic single-stranded oligonucleotides of different nucleic acid sequences according to the present invention are being inserted separately into the compartments of the device (see picture 3) e.g. with the help of a spotter, where they form a monolayer with properties of a liquid-analogue phase. The spreading is such that the lipid molecules point towards the gas phase while the oligonucleotides point into the liquid phase. If required, the aqueous phase may also be covered with a thin layer of oil thus creating a liquid-liquid phase boundary, in which the lipid chains point towards the lipophilic phase.

Now, the target sequence to be identified—marked with reporter groups such as fluorescence dye using methods known in the art in advance—has been injected into the subphase, common to all sample sequences, and spreaded by gentle mechanical stirring. During the adjustment of the chemical equilibrium, the target-DNA will hybridise with the corresponding sequence. The kinetics of the hybridising process may be optimized by adjusting the temperature of the lower section of the device containing the subphase and/or by flow of a buffer solution through the subphase (washing). In a compartment of the device containing the marked target-sequence and the optimum fitting and known sample sequence will form the hybridisation product which can easily be identified by well known methods, like for example fluorescence detectors.

The device used for DNA analyses as schematically illustrated in FIG. 3 may be modified in many ways. Possible modifications concern the number, form and size of the compartments accepting the sample sequences, the volume of the subphase as well as the material of the device. The materials may be plexiglass, stainless steel or quartz glass, just to mention a few. Temperature adjustment of the subphase can easily be done by placing the device into a water bath or by thermoelectrical means (Peltier-element). Therefore, the temperature adjustment can either be done internally or externally.

A preferred embodiment of the device comprises a spotting unit for injecting the nucleolipids having a specific nucleic acid sequence, especially nucleolipids according to this invention, into the individual compartments. Another preferred embodiment of this device includes a unit used to detect the reporter groups which are contained within the hybridisation products between the target- and sample-sequence. The detection unit may be linked to an evaluation unit. This assembly allows for a real time analysis of the hybridising properties and a semi-quantitative or quantitative examination, respectively, of the targeting sequences within the sample to be analysed.

Another embodiment of the present invention comprises a device which can be used for isolating and/or detecting specific nucleic acids. It contains a Wilhelmy plate made from a suitable material such as quartz, ultrapure Si, $TiO_2$, ITO or other materials which can be hydrophobized by coating, e.g. by silanization, and nucleolipids, preferentially nucleolipids according to the invention.

Figure 5:
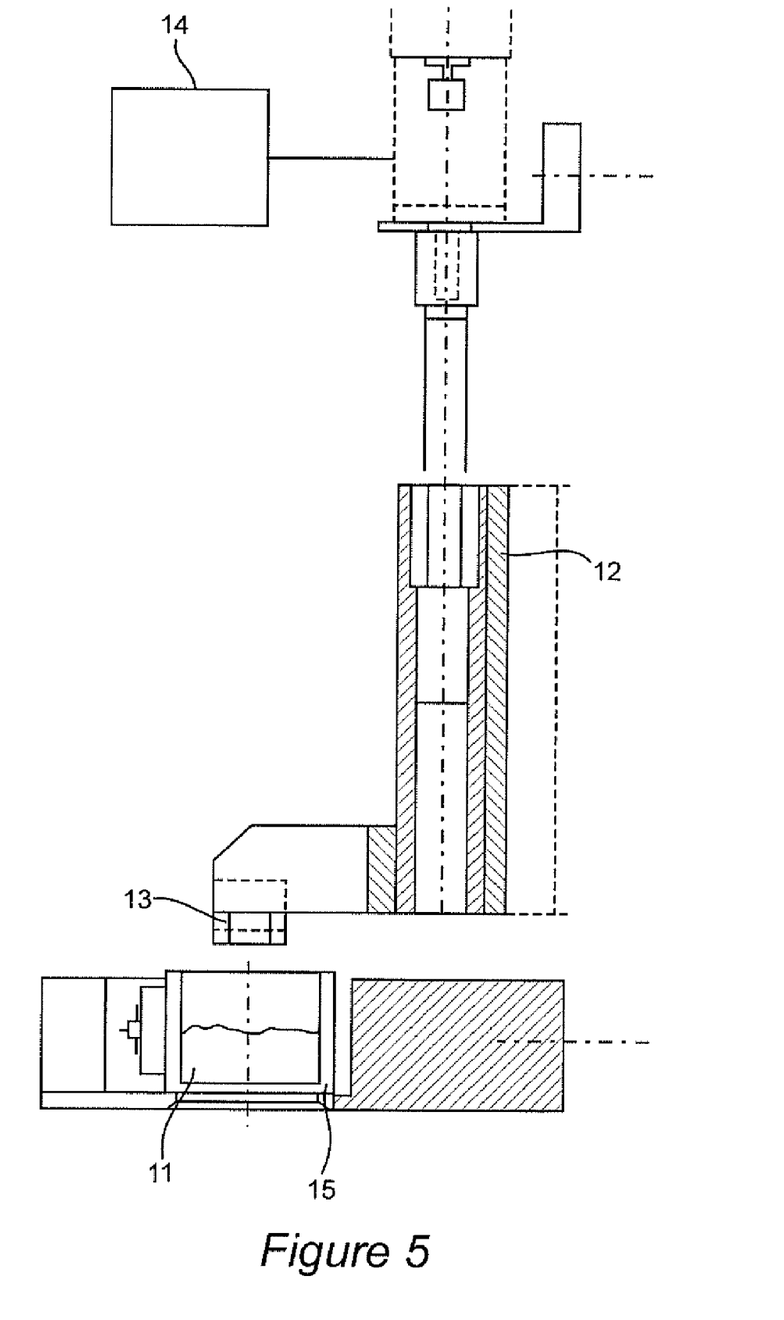
FIG. 5 shows a schematic drawing of a device for the isolation of hybridisation products between target sequences and nucleolipides by means of a dip coater including Wilhelmy-plates.

FIG. 5 shows such a device used for isolation of nucleic acids according to this invention.

The sample containing the nucleic acid is located in a small cavity, here the hutch (11). This cavity is at least partially surrounded by a heating device, such as a Pelltier-element or other temperature adjusting equipment (resistor heater or other known constructions), to permit a heating of the sample thus ensuring a specific hybridisation. Nucleolipids with a predetermined nucleic acid sequence, i.e. those containing a poly(dT) sequence for separating of mRNA, are added to the liquid. The hybridisation products concentrate at the liquid-gaseous boundary, while sample nucleic acids not hybridised remain evenly spreaded within the fluid. Those hybridisation products can be transferred with the help of a movable device (12), like a dip-coater using a solid carrier arranged as an integral part or in two parts like a small plate. This means that the hybridisation products attach to the solid carrier and can be separated from the not-hybridised nucleic acids of the sample. Possible materials for the solid medium or substrate may be for example quartz glass, ultra-clean silicon, $TiO_2$, ITO or other materials which are made hydrophobic by coating, i.e. by silanisation. The lipophilic sections of the nucleolipids attach to the hydrophobic surface of the solid carrier by non-covalent interactions thus allowing a transfer of the hybridisation products and the individual nucleolipids. Control of the immersion and emersion of the carrier can be achieved with a control unit (14). One way of doing this is to have the substrate, e.g. a Wilhelmy-plate, attached to the moveable arm of a dip-coater which is connected to the control unit. The small cavity (like a hutch) may be made of variable materials, but it should not be too hydrophobic in order to avoid the nucleolipids attaching to its surface.

In a preferred embodiment both the emersion/immersion speed of the Wilhelmy-plate and the temperature of the hutch is variable.

There is a big variety when choosing sample nucleic acids.

As discussed above, the reactive lipids according to the present invention are particularly useful for the use in conventional DNA-synthesisers where they may be applied as 5' end building blocks. This allows a simple synthesis of sample sequences and reduces the problems accompanied with the neosynthesis of oligonucleotides on the array itself and the difficult chemical fixation of nucleic acid probes functionalized in advance on the activated surface of the area, respectively.

When selecting a sample nucleic acid, various possibilities are given.

Not only can nature derived DNA- and RNA-molecules be used. Rather oligomeres which can be modified in multiple ways may be used. For example, a PNA (peptide-nucleic acid), complementary to the target nucleic acid to be examined, can be used for hybridisation. Furthermore, nucleic acids with modifications in their sugar moiety, i.e. hexose or hexitole nucleic acids, have been prepared in recent years which are capable of hybridising with natural nucleic acids. Said sample nucleic acids can be used also in the analytic methods according to the present invention. It has been shown that modifying a nucleobase of a sample oligonucleotide, i.e. incorporation of purin-isosteric 8-Aza-7-deaza-7-halo-genopurine-base, significantly increases the stability of a duplex with a common DNA-oligomer which leads to a harmonisation of otherwise differently stable base-pairs guanine-cytosine and adenine-thymine. Also those modified sample nucleic acids can be used in this analytic procedure according to this patent.

According to the present invention, the gaseous phase or the gas is air or an inert gas such as nitrogen, argon etc. According to the present invention, using a system of two fluids which are generally immiscible produces a boundary layer, called liquid-liquid boundary layer. The result is a lipophilic phase as well as a hydrophilic phase. Usually, the target sequence will be in the hydrophilic phase which is generally an aqueous phase, like a buffer solution. The lipophilic phase is for example made up of an organic solvent or oil. The skilled person knows many of those systems.

Another application of the nucleolipids is using them as marker of different compositions, like crude oil or other processed products. Adding nucleolipids with a known nucleic acid sequence specifically marks the products. This specific marking allows for a later identification of the compound's origin. This could be an easy way to identify the polluter of an oil spill. These nucleic acids are soluble in oils and other lipophilic fluids due to their lipophilic section.

The following text gives an example of how the compounds according to the present invention can be synthesised. It is clear that this invention is not only restricted to the mentioned examples.

EXAMPLE

2-Cyanoethyl-2-(dihexadecanylamino)ethyl diisopropylamidophosphane (3)

1 mmol Bis(hexadecanyl)-2-hydroxyethylamine, synthesised from 1-chlorohexadecan and ethanolamine, is being dissolved in anhydrous dichloromethane (25 ml) and mixed with diisopropylamine (330 µl, 1.95 mmol) and chloro-(2-cyanoethoxy) (diisopropyl-amino)phosphine (320 µl, 1.5 mmol). 12 ml of a 5% dilution of $NaHCO_3$ are added after stirring the mixture for 40 minutes at room temperature and the mixture has to be extracted 3 times with dichloromethane (30 ml each). Next, the organic phase has been dried ($Na_2SO_4$), filtered and evaporated. Medium pressure chromatography results in the diasterioisomeric title compound (65%; colourless solid) after evaporation of the main fraction.

$^{31}$P-NMR (CDCl$_3$): δ 148.5, 149.0 ppm. $^1$H-NMR (CDCl$_3$): δ 0.91 (t, J=8 Hz, CH$_3$); 1.29-1.26 (m, CH$_2$); 1.51 (d, J=4 Hz, CH$_3$-iPr); 2.14 (t, J=6 Hz, CH$_2$); 2.32 (t, J=7.2 Hz, CH$_2$-Et); 2.54 (t, J=5.8 Hz, CH$_2$—N); 3.54 (m, CH$_2$); um 4.0 (2 m, CH$_2$).

The invention claimed is:

1. A method for detecting the presence or absence of nucleic acid having specific sequences in a sample comprising the step of:
    a) contacting a sample containing nucleic acids with nucleolipids comprising a lipophilic moiety and oligo- or poly-nucleotide moiety, whereby the oliqo- or poly-nucleotide moiety comprises a sequence which is substantially complementary to a specific sequence of a nucleic acid present in the sample and which hybridizes under hybridizing conditions with the nucleic acid having a specific sequence and the nucleic add present in the sample under hybridizing conditions;
    b) detecting the formation of hybridization products of nucleolipids and a specific sequence of a nucleic acid present in the sample,
        wherein the nucleolipids includes a nucleolipid compound comprising a lipophilic moiety (F) and a nucleoside, oligo- or polynucleotide moiety being connected with each other via a linker (L) and a spacer (S), wherein the linker is an amine group or a molecule having at least two functional groups, being connected with lipophilic moiety, and the nucleoside, oligo- or polynucleotide-moiety is linked via the functional moiety of a phosphoric acid diester.

2. The method according to claim 1 wherein the nucleic acids comprises a reporter group for detection of the hybridization product.

3. The method according to claim 2, wherein the reporter group is a fluorescence dye.

4. A method for detecting the presence or absence of nucleic acid having specific sequences in a sample comprising the step of:
    a) contacting a sample containing nucleic acids with nucleolipids comprising a lipophilic moiety and oligo- or poly-nucleotide moiety, whereby the oligo- or poly-nucleotide moiety comprises a sequence which is substantially complementary to a specific sequence of a nucleic acid present in the sample and which hybridizes under hybridizing conditions with the nucleic acid having a specific sequence and the nucleic add present in the sample under hybridizing conditions;
    b) detecting the formation of hybridization products of nucleolipids and a specific sequence of a nucleic acid present in the sample
        wherein the step of contacting the nucleic acids present in the sample with the nucleolipid is conducted in at least two individual compartments separated from each other, whereby in each of the compartments only nucleolipids with identical nucleoside-, oligo- or polynucleotide-mojeties is present and wherein in the at least two individual compartments different nucleolipids are present.

5. The method according to claim 1, wherein the step of contacting the nucleic acid present in the sample with the nucleolipid is conducted in at least two compartments different from each other, whereby in the individual compartments different samples are present which are immiscible with each other.

6. The method according to claim 1, further comprising the step of washing the hybridization products to remove nucleic acids present in the probe which have not been hybridized.

7. The method according to claim 1 wherein the detection of the hybridization products is conducted by measuring the reporter-group, at a liquid gas interface.

8. The method according to claim 1 wherein the detection of the hybridization products is conducted by measuring the reporter group at a liquid-liquid interface of an aqueous-hydrophilic and a lipophilic liquid.

9. The method according to claim 4 wherein the nucleic acids comprises a reporter group for detection of the hybridization product.

10. The method according to claim 9 wherein the reporter group is a fluorescence dye.

11. The method according to claim 4 wherein in the at least two individual compartments different samples are present which are immiscible with each other.

12. The method according to claim 4 further comprising the step of washing the hybridization products to remove nucleic acids present in the probe which have not been hybridized.

13. The method according to claim 4 wherein the detection of the hybridization products is conducted by measuring the reporter-group at a liquid gas interface.

14. The method according to claim 4 wherein the detection of the hybridization products is conducted by measuring the reporter group at the liquid-liquid interface of an aqueous-hydrophilic and a lipophilic liquid.

* * * * *